United States Patent
Prior et al.

(10) Patent No.: US 11,553,958 B2
(45) Date of Patent: Jan. 17, 2023

(54) ELECTROSURGICAL DEVICE FOR CUTTING TISSUE

(71) Applicant: Covidien LP, Mansfield, MA (US)

(72) Inventors: Scott J. Prior, Shelton, CT (US); Brian J. Creston, Madison, CT (US); Christopher M. Meehan, New Haven, CT (US); Amy Kung, Hamden, CT (US); Ernest A. Addi, Middletown, CT (US); Jacob C. Baril, Norwalk, CT (US); Thomas A. Zammataro, North Haven, CT (US); Saumya Banerjee, Hamden, CT (US); Ronald L. Green, Bethel, CT (US)

(73) Assignee: Covidien LP, Mansfield, MA (US)

( * ) Notice: Subject to any disclaimer, the term of this patent is extended or adjusted under 35 U.S.C. 154(b) by 392 days.

(21) Appl. No.: 16/784,988

(22) Filed: Feb. 7, 2020

(65) Prior Publication Data

US 2021/0244460 A1    Aug. 12, 2021

(51) Int. Cl.
*A61B 18/14* (2006.01)
*A61B 18/00* (2006.01)
*A61B 18/12* (2006.01)

(52) U.S. Cl.
CPC .. *A61B 18/149* (2013.01); *A61B 2018/00083* (2013.01); *A61B 2018/00184* (2013.01); *A61B 2018/00601* (2013.01); *A61B 2018/126* (2013.01); *A61B 2018/144* (2013.01);
(Continued)

(58) Field of Classification Search
CPC .......... A61B 18/149; A61B 2018/1407; A61B 2018/1412; A61B 2018/00083; A61B 2018/00601; A61B 2018/126; A61B 2018/144; A61B 2018/00184
See application file for complete search history.

(56) References Cited

U.S. PATENT DOCUMENTS

| | | | |
|---|---|---|---|
| 5,403,310 A * | 4/1995 | Fischer | A61B 10/0291 606/49 |
| 5,702,438 A * | 12/1997 | Avitall | A61N 1/056 607/128 |
| 5,766,167 A | 6/1998 | Eggers et al. | |

(Continued)

FOREIGN PATENT DOCUMENTS

| AU | 7086087 A | 10/1987 |
|---|---|---|
| DE | 202004006102 U1 | 7/2004 |

(Continued)

*Primary Examiner* — Joanne M Hoffman
*Assistant Examiner* — Sean W Collins
(74) *Attorney, Agent, or Firm* — Carter, DeLuca & Farrell LLP

(57) ABSTRACT

A tool assembly for use with an electrosurgical device for cutting tissue includes a base portion, a return lead, an electrical insulator, a center pin, and an active lead. The center pin extends from the base portion and through a lumen of the electrical insulator. The active lead is securely fixed to the base portion and extends between the base portion and a distal portion of the center pin such that a portion of the active lead extends around the distal portion of the center pin and first and second segments of the active lead are spaced apart from the return lead. Upon activation, electrosurgical energy is transmitted from the active lead through tissue to the return lead to cut tissue in contact with the active lead.

20 Claims, 10 Drawing Sheets

(52) U.S. Cl.
    CPC .............. *A61B 2018/1407* (2013.01); *A61B 2018/1412* (2013.01)

(56) References Cited

U.S. PATENT DOCUMENTS

| | | | |
|---|---|---|---|
| 6,068,603 | A | 5/2000 | Suzuki |
| 6,267,759 | B1 | 7/2001 | Quick |
| 6,730,085 | B2 | 5/2004 | George et al. |
| 7,156,844 | B2 | 1/2007 | Reschke et al. |
| 9,463,059 | B2 | 10/2016 | Suon et al. |
| 2002/0049441 | A1* | 4/2002 | George .............. A61B 18/1485 600/564 |
| 2009/0062793 | A1 | 3/2009 | Eliachar et al. |
| 2010/0268224 | A1* | 10/2010 | Landon .............. A61B 18/1402 606/50 |
| 2013/0255063 | A1 | 10/2013 | Hart et al. |
| 2013/0267947 | A1 | 10/2013 | Orszulak |

FOREIGN PATENT DOCUMENTS

| | | |
|---|---|---|
| WO | 2006068808 A1 | 6/2006 |
| WO | 2018187244 A3 | 3/2019 |

\* cited by examiner

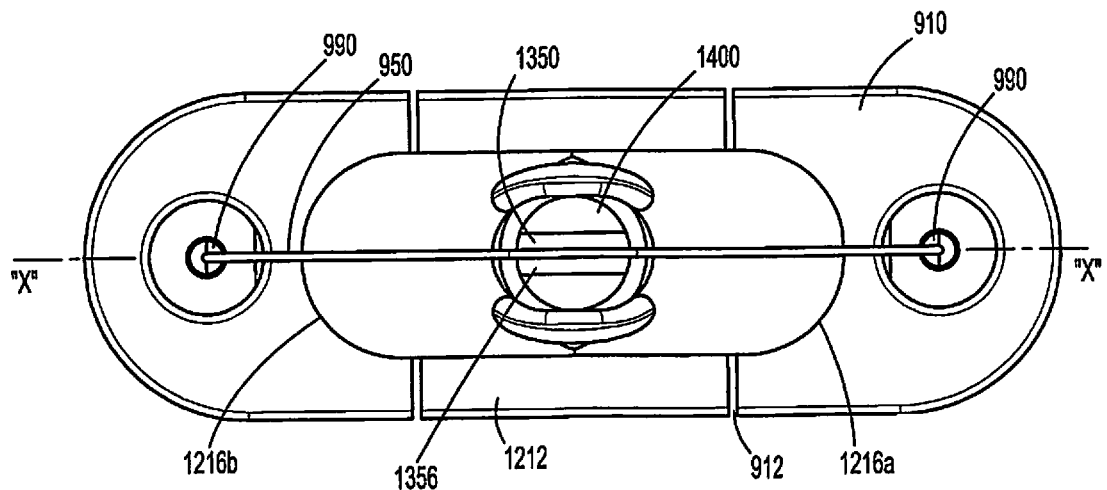
FIG. 8
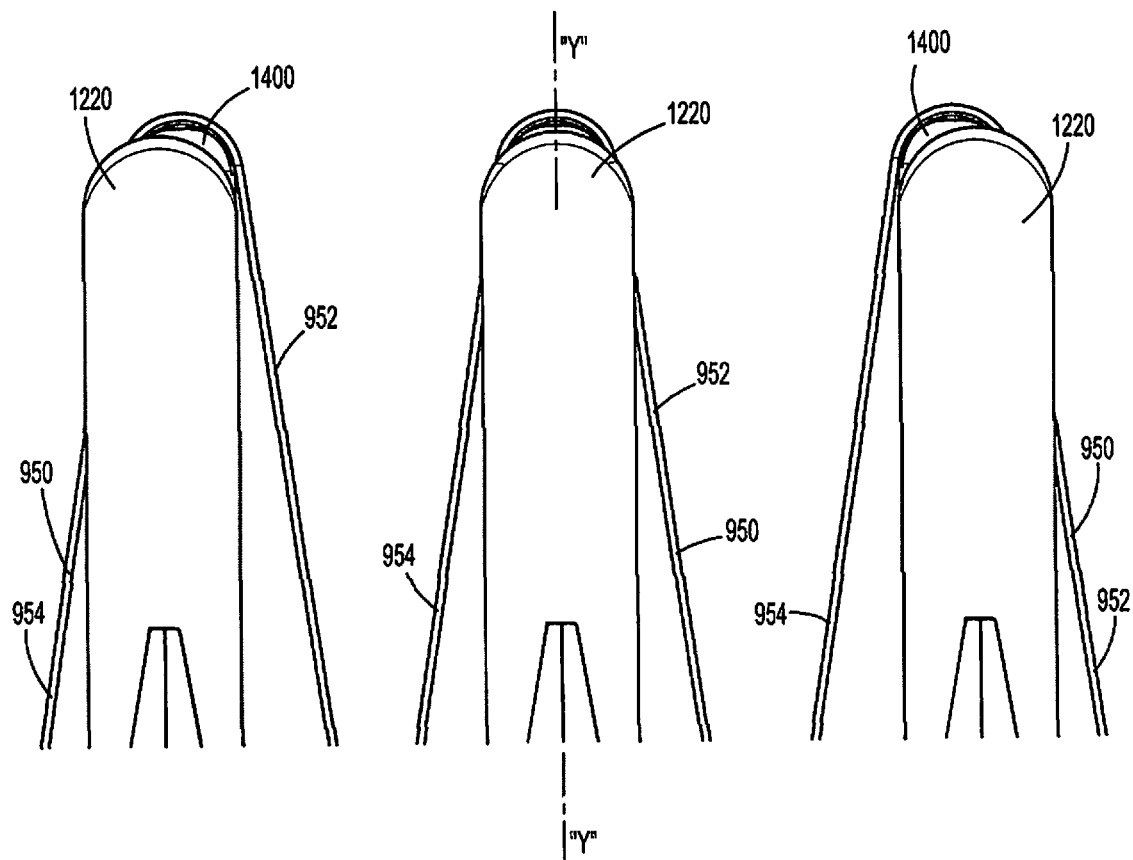
FIG. 9     FIG. 10     FIG. 11

ELECTROSURGICAL DEVICE FOR CUTTING TISSUE

FIELD

The present disclosure relates to surgical devices and, more particularly, to bipolar electrosurgical devices for cutting tissue.

BACKGROUND

Laparoscopic surgery is increasingly common. The principle of laparoscopic surgery is to perform a surgical procedure with small keyhole incisions. Usually, two or three such keyhole incisions are made in the abdomen for insertion of a telescopic video camera, laparoscopic instruments, and/or electrosurgical devices. Electrosurgical devices are used in both open surgical and laparoscopic surgical procedures to cut and/or coagulate tissue. Various types of electrosurgical devices are known, including those that use diathermy with either monopolar or bipolar current, and advanced devices such as harmonic scissors and argon beam and laser devices. Monopolar and bipolar devices use one or two electrodes, respectively, to deliver electrical energy from a current source to the surgical site. By varying the voltage, current, or waveform of the electrical energy delivered by the electrode, surgeons can cut tissue, coagulate tissue to stop bleeding, or produce a "blended cut" that combines these two functions.

SUMMARY

As used herein, the term "distal" refers to the portion that is being described which is further from a user, while the term "proximal" refers to the portion that is being described which is closer to a user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

In accordance with an aspect of the present disclosure, a tool assembly for use with an electrosurgical device for cutting tissue including a base portion, a return lead adapted to be electrically coupled to a return terminal, an electrical insulator, a center pin, and an active lead adapted to be electrically coupled to an active terminal. The return lead includes a body defining a bore therethrough. The electrical insulator extends through the bore of the body. The electrical insulator defines a lumen. The center pin extends from the base portion and through the lumen of the electrical insulator. The active lead is securely fixed to the base portion and extends between the base portion and a distal portion of the center pin such that a portion of the active lead extends around the distal portion of the center pin and first and second segments of the active lead are spaced apart from the return lead. Upon activation, electrosurgical energy is transmitted from the active lead through tissue to the return lead to cut tissue in contact with the active lead.

In an aspect of the present disclosure, the distal portion of the center pin may extend distally from the lumen of the electrical insulator.

In another aspect of the present disclosure, the return lead may include a tapered portion and an elongate portion extending distally from the tapered portion.

In yet another aspect of the present disclosure, the tapered portion of the return lead may include opposing first and second surfaces. The first and second segments of the active lead may be spaced apart from the respective opposing first and second surfaces of the return lead.

In still another aspect of the present disclosure, at least one of the opposing first and second surfaces may define an acute angle with respect to a longitudinal axis defined by the tool assembly.

In still yet another aspect of the present disclosure, the active lead may be a wire.

In another aspect of the present disclosure, the distal portion of the center pin may define a groove configured to guide the portion of the active lead therethrough.

In another aspect of the present disclosure, the elongate portion may define opposing lateral slots configured be in registration with the respective first and second segments of the active lead.

In yet another aspect of the present disclosure, the electrical insulator may be formed of ceramic.

In still yet another aspect of the present disclosure, the return lead may be formed of stainless steel.

In still yet another aspect of the present disclosure, the electrical insulator may be securely fixed with the base portion.

In still yet another aspect of the present disclosure, the return lead may be movable relative to the active lead.

In still yet another embodiment, the return lead may be slidable in a direction orthogonal to a longitudinal axis defined by the tool assembly.

In accordance with another aspect of the present disclosure, a tool assembly for use with an electrosurgical device for cutting tissue includes an active lead adapted to be electrically coupled to a first electrical potential, an electrical insulator, and a return lead adapted to be electrically coupled to a second electrical potential. The active lead includes a stem portion and a wire portion distal of the stem portion. The electrical insulator is coupled to the stem portion of the active lead. The electrical insulator includes opposing first and second arms and a distal portion defining opposing first and second grooves such that a first segment of the active lead extends out of the first groove and into the first arm and a second segment of the active lead extends out of the second groove and into the second arm. The return lead is configured to receive the electrical insulator therein. The return lead defines an aperture configured to receive a portion of the electrical insulator therethrough, and opposing slots configured to receive the respective opposing first and second arms of the electrical insulator such that the first and second segments of the active lead are laterally spaced apart from the return lead. Upon activation, electrosurgical energy is transmitted between the first and second electrical potentials and through tissue disposed therebetween.

In an aspect of the present disclosure, the electrical insulator may define first and second channels extending along a length thereof. The first and second channels may be configured to receive the respective first and second segments of the active lead.

In another aspect of the present disclosure, at least one of the first or second segments of the active lead may define an acute angle with respect to a longitudinal axis defined by the tool assembly.

In still another aspect of the present disclosure, the electrical insulator may be formed of ceramic.

In an aspect of the present disclosure, the tool assembly may further include a sleeve configured to receive a portion of the stem portion of the active lead and a portion of the electrical insulator. The portion of the sleeve may be configured to be received within the return lead.

In another aspect of the present disclosure, the return lead may include a tapered profile including opposing surfaces in registration with the first and second segments of the active lead.

In yet another aspect of the present disclosure, the active lead may be a wire.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

FIG. 8 is a top view of the tool assembly of FIG. 7;

FIGS. 9-11 are partial side views of the distal portion of the tool assembly of FIG. 7 illustrating lateral displacement of a return lead relative to an active lead;

DETAILED DESCRIPTION

Figure 1:
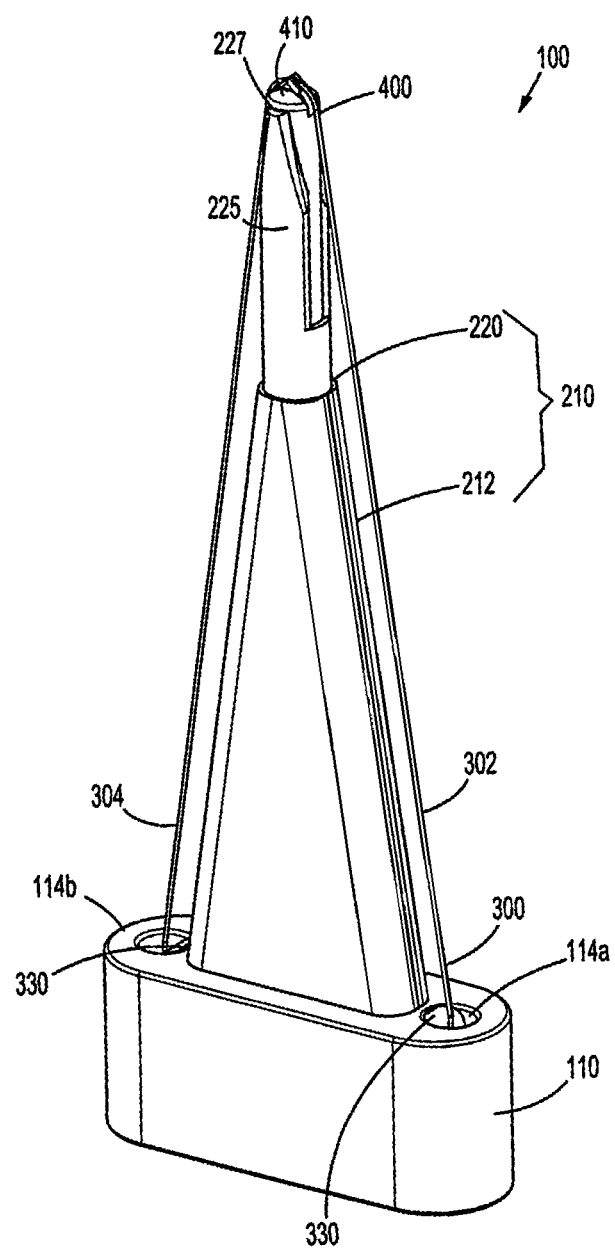
FIG. 1 is a perspective view of a tool assembly for use with an electrosurgical device in accordance with an aspect of the present disclosure.

Turning now to FIG. 1, a tool assembly for use with an electrosurgical device in accordance with an aspect of the present disclosure is generally shown as a tool assembly 100 adapted to be electrically coupled to an electrosurgical energy source such as, e.g., a generator (not shown), to provide bipolar radio-frequency (RF) power output. The electrosurgical energy source may include electronic circuitry configured to generate radio frequency energy specifically suited for various electrosurgical modes and/or procedures. The electrosurgical energy source may include one or more converting devices for converting from DC to AC or vice versa. The electrosurgical device may be configured to transmit any suitable electric current (e.g., AC and/or DC) at any suitable frequency. For a detailed discussion of the construction and operation of exemplary electrosurgical devices and electrosurgical energy sources, reference may be made to U.S. Patent Publication Nos. 2013/0267947 and 2013/0255063; and U.S. Pat. Nos. 7,156,844 and 5,766,167, the entire contents of each of which are incorporated by reference herein.

Figure 2:
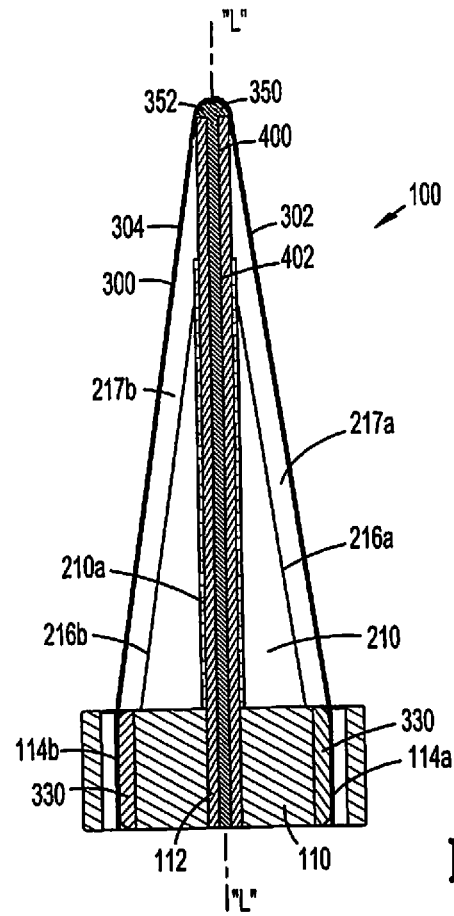
FIG. 2 is a side cross-sectional view of the tool assembly of FIG. 1.

With reference to FIGS. 1 and 2, the tool assembly 100 is coupled (releasably or integrally) to a body portion (not shown), e.g., a handpiece, of an electrosurgical device. The tool assembly 100 includes a base portion 110, formed of or coated with an electrically-insulative material, supporting a return lead 210 electrically coupled to an electrosurgical energy source (e.g., via a return terminal), and an active lead 300 electrically coupled to the electrosurgical energy source (e.g., via an active terminal). For example, the body portion of the electrosurgical device may include a switch to control electrical communication between the electrosurgical energy source and the active lead 300 for selectively activating the active lead 300 to cut tissue. The return lead 210 serves as an electrical return for electrosurgical energy (e.g., electric current) conducted through the active lead 300. In embodiments, tool assembly 100 is configured to connect to a robotic arm of a robotic surgical system to enable manipulation and control thereof.

With continued reference to FIGS. 1 and 2, the base portion 110 defines a central bore 112 and opposing lateral bores 114a, 114b. The return lead 210 includes a first body portion 212 coupled to the base portion 110, and a second body portion 220 extending distally from the first body portion 210. In particular, the first body portion 212 has, e.g., a tapered profile, along a longitudinal axis "L-L" defined by the return lead 210, and the second body portion 220 has an elongate, e.g., generally cylindrical, profile extending along the longitudinal axis "L-L". In embodiments, the first and second body portions 212, 220 may be formed as a single construct. In other embodiments, the first and second body portions 212, 220 may be monolithically formed of stainless steel. The return lead 210 defines a bore 210a extending along the longitudinal axis "L-L" thereof. In particular, the bore 210a is configured to receive an electrical insulator 400 therein and a center pin 350 nested within the electrical insulator 400. The bore 210a of the return lead 210 is axially aligned with and in communication with the central bore 112 of the base portion 110 to receive the electrical insulator 400 and the center pin 350 therein. The first body portion 212 includes opposing surfaces 216a, 216b defining respective acute angles with the longitudinal axis "L-L." In embodiments, the opposing surfaces 216a, 216b may be symmetric with respect to the longitudinal axis "L-L." The second body portion 220 defines lateral slots 225 exposing the electrical insulator 400 disposed in the bore 210a of the return lead 210, and a distal opening 227 (FIG. 3) through which a distal end portion 410 of the electrical insulator 400 extends.

Figure 3:
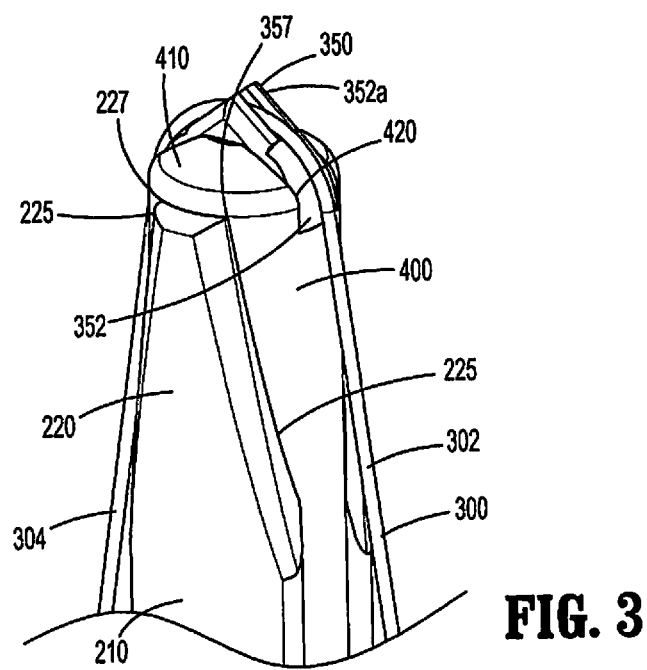
FIG. 3 is a partially enlarged perspective view of the tool assembly of FIG. 1.

With reference to FIG. 3, the electrical insulator 400 extends through the central bore 112 of the base portion 110 and the bore 210a of the return lead 210. In embodiments, the electrical insulator 400 may be secured with the base portion 110 and the return lead 210 by, e.g., friction fit, ultrasonic welding, etc. In particular, the electrical insulator 400 includes the distal end portion 410 at least partially protruding through the distal opening 227 of the second body portion 220 of the return lead 210. The electrical insulator 400 defines a lumen 402 (FIG. 2) extending along a length thereof, and a distal slot 420. The lumen 402 is configured to receive the center pin 350 therein. The center pin 350 extends from the base portion 110 and through the distal slot 420 of the electrical insulator 400. In particular, a tip portion 352a of the distal portion 352 of the center pin 350 protrudes through the distal slot 420. The tip portion 352a has, e.g., a tapered profile, and defines a groove 357 configured to support a portion of the active lead 300 therein.

With reference back to FIGS. 1-3, the active lead 300 may be formed of a single strand metal wire such as, e.g., tungsten wire. The wire of the active lead 300 has a relatively small surface area compared to the relatively large surface area of the return lead 210 to provide high efficiency in cutting tissue. The active lead 300 includes first and second segments 302, 304 having respective first and second ends received in the respective lateral bores 114a, 114b of the base portion 110. In particular, the first and second ends are securely anchored in the respective lateral bores 114a, 114b by respective anchor pins 330. The anchor pins 330 and the center pin 350 are in electrical communication with the active terminal of the electrosurgical energy source to supply electrosurgical energy to the active lead 300. A portion of the active lead 300 is placed in the groove 357 of the center pin 350 such that the groove 357 supports the active lead 300 looping around the distal portion 352 of the center pin 350. The first and second segments 302, 304 of the active lead 300 extend from the groove 357 towards the respective lateral bores 114a, 114b of the base portion 110. Under such a configuration, the first and second segments 302, 304 of the active lead 300 wrap around the second body portion 220 of the return lead 210 such that portions of the first and second segments 302, 304 of the return lead 210 are in registration with the respective lateral slots 225 of the return lead 210 and portions of the electrical insulator 400 exposed through the lateral slots 225. Further, the first and second segments 302, 304 of the return lead 310 are in registration with the respective surfaces 216a, 216b of the return lead 210, and define gaps 217a, 217b with the respective surfaces 216a, 216b. The active lead 300 is under tension such that the active lead 300 is spaced apart from the exterior of the electrical insulator 400. When the active lead 300 engages tissue, the active lead 300 does not deflect or sag while cutting tissue. Such a configuration facilitates plunge cutting of tissue.

Any portion of the return lead 210 may serve as an electrical return for electrosurgical energy (e.g., electric current) conducted through the first or second segments 302, 304 of the active lead 300. A large surface area of the return lead 210 compared to the small surface area of the active lead 300 may provide a desirable ratio of return surface area to cutting surface area for high efficiency in cutting tissue. The return lead 210 may contact tissue at approximately the same time as, e.g., at least one of the first or second segments 302, 304 of the active lead 300, and thus allowing it to cut tissue. The return lead 210 returns the electrosurgical energy to the electrosurgical energy source. In this manner, the electrosurgical energy applied via the first or second segments 302, 304 across tissue severs tissue in contact with either or both of the first or second segments 302, 304.

In embodiments, the electrical insulator 400 may be formed of a ceramic material due to its hardness and inherent ability to withstand high temperature fluctuations. Alternatively, the electrical insulator 400 may be made from a material having a high Comparative Tracking Index (CTI) having a value in the range of about 300 to about 600 volts. Examples of high CTI materials include nylons and syndiotactic polystryrenes such as QUESTRA® manufactured by DOW Chemical. Other materials may also be utilized either alone or in combination, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

In use, a clinician may position the tool assembly 100 operatively coupled to an electrosurgical device adjacent a target tissue. In order to cut tissue from a surgical site, the electrosurgical device 100 is activated by actuating the switch to supply electrosurgical energy to the active lead 300. Activation of the electrosurgical device draws the electrosurgical energy from the electrosurgical energy source to the active lead 300. For example, the second body portion 220 is configured to contact tissue at approximately the same time as the first or second segment 302, 304 of the active lead 300, and thus performing a cut in tissue. The return lead 210 returns the electrosurgical energy to the electrosurgical energy source via the return terminal of the electrosurgical energy source. Under such a configuration, the electrosurgical energy applied via the active lead 300 across tissue severs the tissue. This process may be repeated as necessary. After tissue is removed, the clinician may coagulate and/or cauterize the tissue to control bleeding, if necessary.

Figure 4:
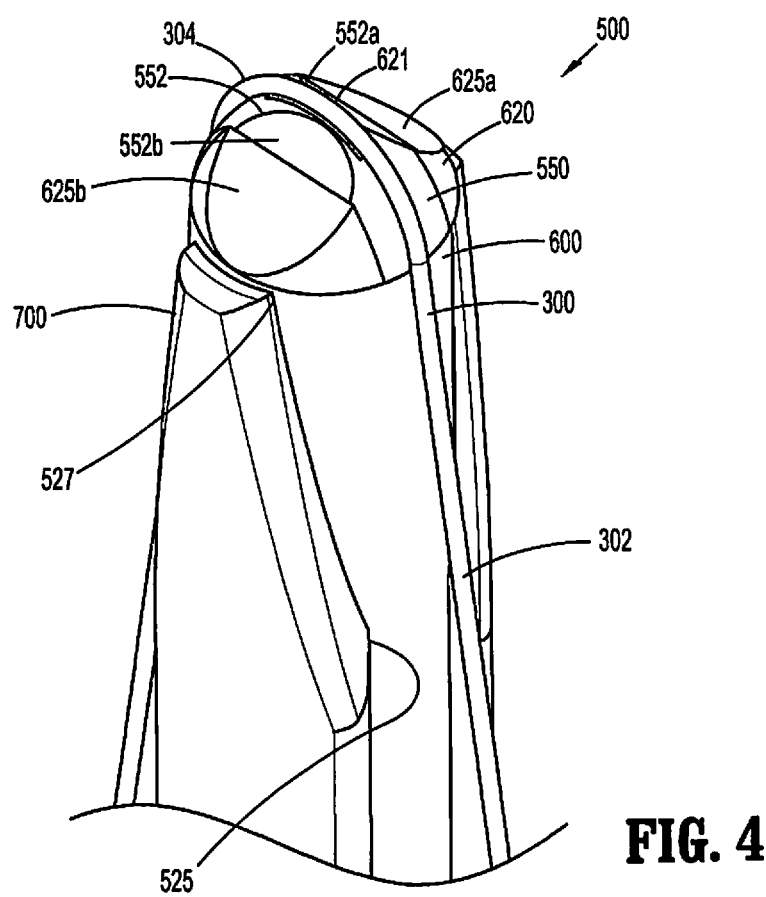
FIG. 4 is a partial perspective view of a distal portion tool assembly in accordance with another aspect of the present disclosure.

With reference now to FIG. 4, it is also contemplated that a tool assembly 500 may include a center pin 550 having a distal end portion 552. The distal end portion 552 may include opposing tapered surface 552a, 552b. A portion of the active lead 300 extends between the opposing tapered surfaces 552a, 552b. The first and second segments 302, 304 wrap around the distal end portion 552 of the center pin 550 and extend proximally over respective lateral slots 525 (only one shown in FIG. 4) such that the active lead 300 is spaced apart from a return lead 700. In addition, the electrical insulator 600 includes a distal end portion 620 protruding from a distal opening 527 defined by the return lead 700. The distal end portion 620 defines a slot 621 configured to receive at least a portion of the distal end portion 552 of the center pin 550. In particular, the distal end portion 620 of the electrical insulator 600 includes opposing tapered surfaces 625a, 625b being flush with the respective tapered surfaces 552a, 552b of the center pin 550. Such a configuration facilitates insertion of the tool assembly 500 through cavities or incisions to reach the surgical site. Tool assembly 500 may otherwise be configured similar to tool assembly 100 (FIG. 1)

Figure 5:
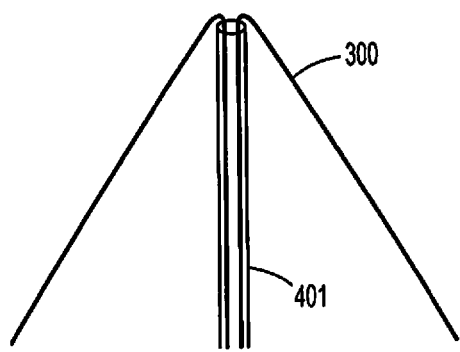
FIGS. 5 and 6 are side cross-sectional views of distal portions of tool assemblies for use with an electrosurgical device in accordance with other aspects of the present disclosure.
Figure 6:
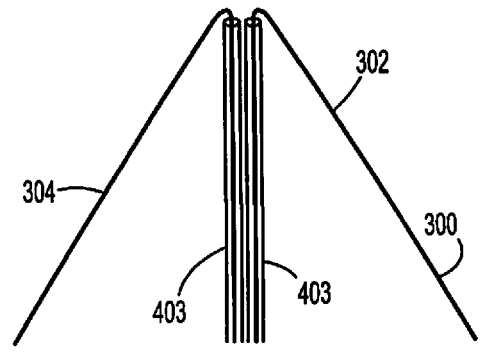

While the tool assemblies 100, 500 utilize the center pins 350, 550 to electrically couple the active lead 300 to the electrosurgical energy source, it is also contemplated that an active lead 300 may be looped through an electrical insulator 401 as shown in FIG. 5. The electrical insulator 401 may have a tubular configuration. In particular, both the first and second segments 302, 304 of the active lead 300 may be looped through a single electrical insulator 401. However, it is further contemplated that the first and second segments 302, 304 of the active lead 300 may be looped through separate electrical insulators 403 as shown in FIG. 6.

Figure 7:
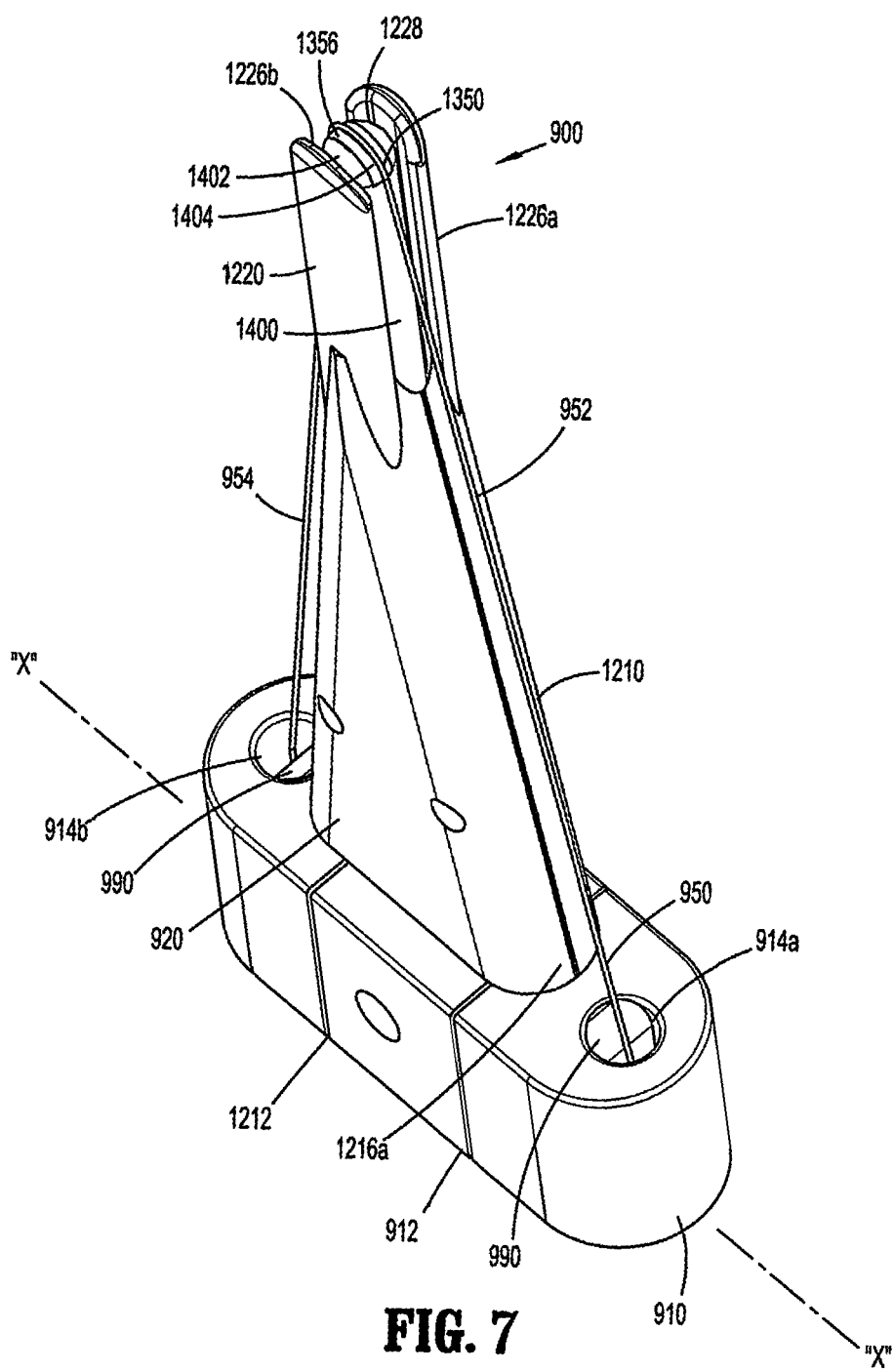
FIG. 7 is a perspective view of a tool assembly for use with an electrosurgical device in accordance with yet another aspect of the present disclosure.
Figure 12:
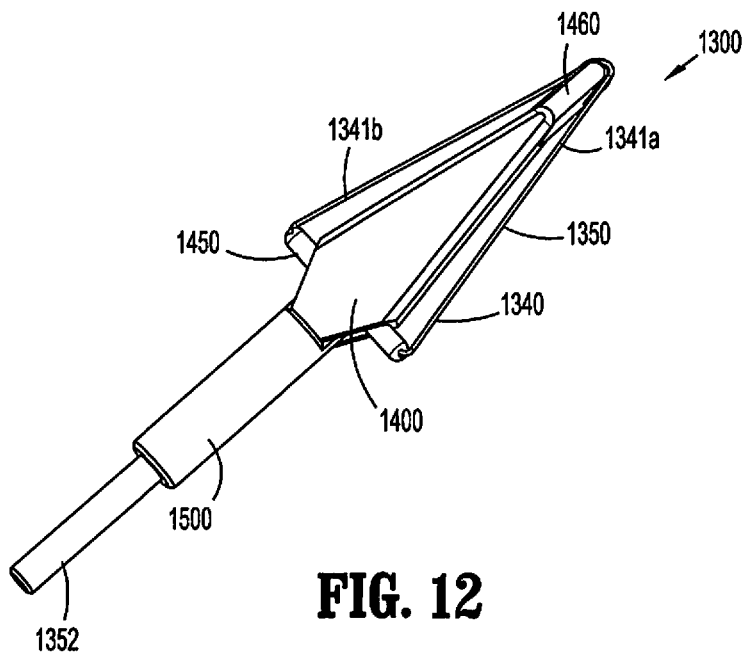
FIG. 12 is a perspective view of a tool assembly for use with an electrosurgical device in accordance with another aspect of the present disclosure.

With reference now to FIGS. 7 and 8, there is provided a tool assembly 900 for use with an electrosurgical device in accordance with another aspect of the present disclosure. In the interest of brevity, portions of the tool assembly 900 substantially similar to the portion of the tool assemblies 100, 500 will not be described herein to avoid obscuring the present disclosure in unnecessary detail. The tool assembly 900 is adapted to be coupled to a body portion of an electrosurgical device to cut tissue. The tool assembly 900 includes a return lead 920, a base portion 910 slidably supporting the return lead 920 electrically coupled to the electrosurgical energy source (e.g., via a return terminal), and an active lead 950 electrically coupled to the electrosurgical energy source (e.g., via an active terminal). In contrast to the tool assemblies 100, 500, the return lead 920 is movable relative to the active lead 950 to facilitate engagement of the active lead 950 with tissue to be cut, as will be described below.

The base portion 910 defines a central cavity 912 and opposing lateral bores 914a, 914b. The return lead 920 includes a slidable member 1212, a first body portion 1210 coupled to the slidable member 1212, and a second body portion 1220 extending distally from the first body portion 1210. The return lead 920 serves as an electrical return for electrosurgical energy (e.g., electric current) conducted through the active lead 950. The first body portion 1210 is coupled to the slidable member 1212 to move as a single construct along a lateral axis "X-X" (FIG. 7) orthogonal to the longitudinal axis "Y-Y" (FIG. 10). The return lead 920 defines a channel (not shown) extending along the longitudinal axis "Y-Y" thereof. In particular, the channel is configured to receive an electrical insulator 1400 and a center pin 1350 therein. In embodiments, the electrical insulator 1400 may be formed of a ceramic material due to its hardness and inherent ability to withstand high temperature fluctuations. Alternatively, the electrical insulator 1400 may be made from the materials described hereinabove with respect to the electrical insulator 400.

The electrical insulator 1400 is fixedly coupled with the base portion 910 such that the electrical insulator 1400, e.g., bisects the base portion 910. The second body portion 1220 of the return lead 920 defines a distal opening 1228 and opposing lateral slots 1226a, 1226b. The electrical insulator 1400 includes a distal end portion 1402 having, e.g., a hemispherical profile. The distal end portion 1402 further defines a slot 1404 configured to receive a distal portion 1356 of the center pin 1350 extending from the base portion 910 and electrically coupled with the electrosurgical energy source. The distal portion 1356 of the center pin 1350 received in the slot 1404 of the electrical insulator 1400 may have a profile conforming to a curvature of the distal end portion 1402 of the electrical insulator 1400. However, the distal end portion 1356 of the center pin 1350 may define a groove configured to receive a portion of the active lead 950 therein. The active lead 950 may be formed of a single strand metal wire such as, e.g., tungsten wire. A portion of the active lead 950 is wrapped around the groove of the distal end portion 1356 of the center pin 1350 such that the first and second segments 952, 954 of the active lead 950 are directed towards the respective lateral bores 914a, 914b.

With particular reference now to FIGS. 8 and 9, the active lead 950 is a wire, e.g., a single strand tungsten wire. The small surface area of the wire relative to a large surface area of the return lead 920 provides high efficiency in cutting tissue. The anchoring members 990 and the center pin 1350 are electrically coupled to the active terminal of the electrosurgical energy source to supply electrosurgical energy to the active lead 950. The active lead 950 may be in tension such that when the active lead 950 engages tissue, the active lead 950 does not deflect or sag while cutting tissue.

The first body portion 1210 has, e.g., a tapered profile along the longitudinal axis "Y-Y," and the second body portion 1220 has an elongate profile aligned with the longitudinal axis "Y-Y." The first body portion 212 includes opposing surfaces 1216a, 1216b defining respective acute angles with the longitudinal axis "Y-Y." In embodiments, the first and second body portions 1210, 1220 may be formed as a single construct. In other embodiments, the first and second body portions 1210, 1220 may be monolithically formed of stainless steel. Under such a configuration, the active lead 950 extending between the distal end portion 1356 of the center pin 1350 and the respective lateral bores 914a, 914b, is spaced apart from the respective opposing surfaces 1216a, 1216b. In addition, the first and second segments 952, 954 of the active lead 950 extend through the respective lateral slots 1226a, 1226b of the second body portion 1220. Under such a configuration, the active lead 950 is spaced apart from the return lead 920.

With reference now to FIGS. 8-11, the slidable member 1212 is disposed within the central cavity 912 of the base portion 910. Specifically, the slidable member 1212 is movable along the lateral axis "X-X" orthogonal to the longitudinal axis "Y-Y." The central cavity 912 is dimensioned to enable predetermined amount of lateral displacement of the slidable member 1212 such that the lateral displacement of the slidable member 1212 causes the first or second segment 952, 954 of the active lead 950 to be spaced apart from the corresponding lateral slot 1226a, 1226b (FIG. 7) of the return lead 920, depending on the direction of the lateral displacement. The active lead 950 along with the electrical insulator 1400 and the center pin 1350 are securely fixed with the base portion 910. Thus, depending on the movement of the slidable member 1212 relative to the active lead 950, the second body portion 1220 may be displaced away from one of the first or second segments 952, 954 of the active lead 950.

With particular referenced to FIGS. 9-11, when the portions of the first or second segment 952, 954 of the active lead 950 engage tissue to be cut, the second body portion 1220 may be pushed against the surrounding tissue. When the active lead 950 is further pushed into tissue, the second body portion 1220 is displaced away from the tissue, which, in turn, exposes the portion of active lead 950 engaging tissue out of the corresponding lateral slot 1226a, 1226b. Under such a configuration, lateral displacement of the return lead 1220 facilitate cutting of tissue by the active lead 950. In this manner, the return lead 920 is transitionable from a neutral state (FIG. 10), in which, the return lead 920 is in a generally centered position with respect to the first and second segments 952, 954 of the active lead 950. The return lead 920 may be displaced laterally in opposite directions as shown in FIGS. 9 and 11. In embodiments, the return lead 920 may be biased towards the neutral position.

In embodiments, the return lead 920 may be monolithically formed of stainless steel. Accordingly, any portion of the return lead 920 may serve as an electrical return for electrosurgical energy (e.g., electric current) conducted through the first or second segments 952, 954 of the active lead 950. For example, the return lead 920 may contact tissue at approximately the same time as, e.g., at least one of the first or second segments 952, 954 of the active lead 950, and thus allowing it to cut. The return lead 920 returns the electrosurgical energy to the electrosurgical energy source. In this manner, the electrosurgical energy applied via the first or second segments 952, 954 of the active lead 950 across tissue severs tissue in contact with either or both of the first or second segments 952, 954. The use and operation of the tool assembly 900 is otherwise substantially similar to the use and operation of the tool assemblies described hereinabove, and thus is not be described herein.

With reference now to FIGS. 12-15, another tool assembly for use with an electrosurgical device in accordance with an embodiment of the present disclosure is shown generally as a tool assembly 1300. In the interest of brevity, portions of the tool assembly 1300 substantially similar to the portion of the tool assemblies 100, 500, 900 will not be described herein to avoid obscuring the present disclosure in unnecessary detail. The tool assembly 1300 includes an active lead 1350, a return lead 1400, an electrical insulator 1450, and a sleeve 1500. The active lead 1350 includes a stem portion 1352 electrically coupled to the active terminal of the electrosurgical energy source, and a wire portion 1340 coupled to the stem portion 1352. The stem 1352 includes a neck portion 1354 configured to be coupled with the electrical insulator 1450. The wire portion 1340 may be a single strand wire such as, e.g., a tungsten wire. The small surface area of the wire relative to the large surface area of the return lead 1400 provides high efficiency in cutting tissue.

Figure 13:
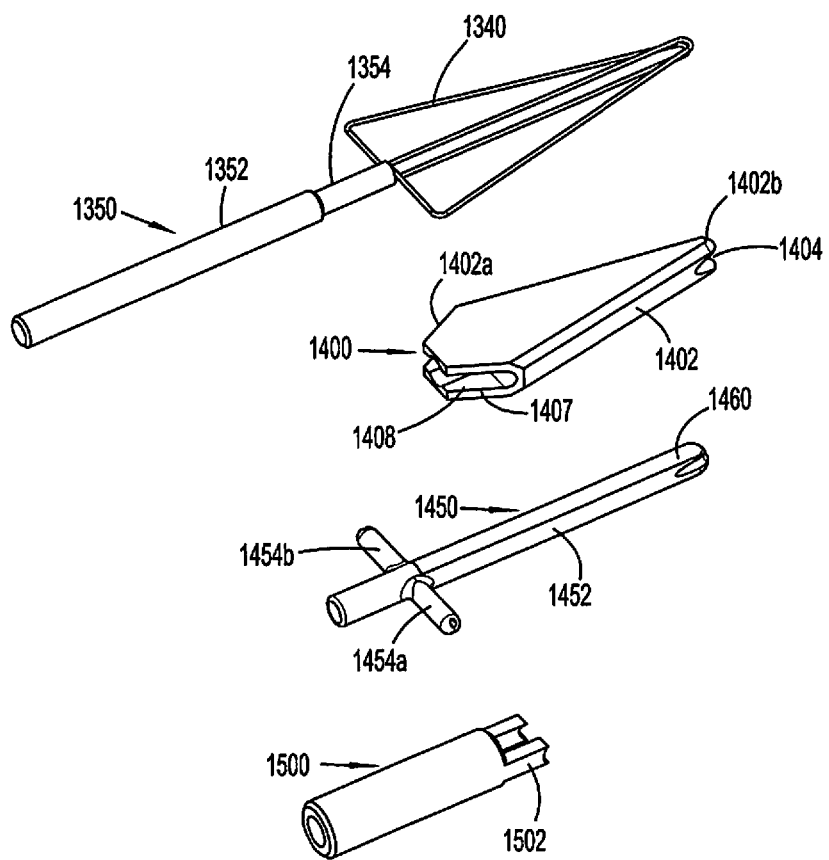
FIG. 13 is an exploded perspective view of the tool assembly of FIG. 12 with parts separated.

With particular reference to FIG. 13, the electrical insulator 1450 includes a tubular body 1452 defining first and second channels (not shown) extending along a length thereof, and opposing lateral arms 1454a, 1454b in communication with the respective first and second channels. The wire portion 1340 of the active lead 1350 extends through the first and second channels and the opposing lateral arms 1454a, 1454b.

Figure 14:
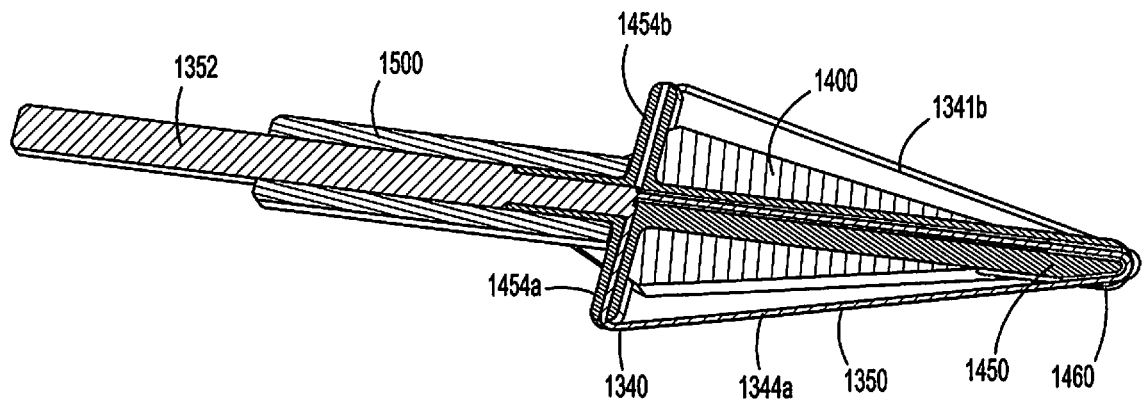
FIG. 14 is a cross-sectional view of the tool assembly of FIG. 12.
Figure 15:
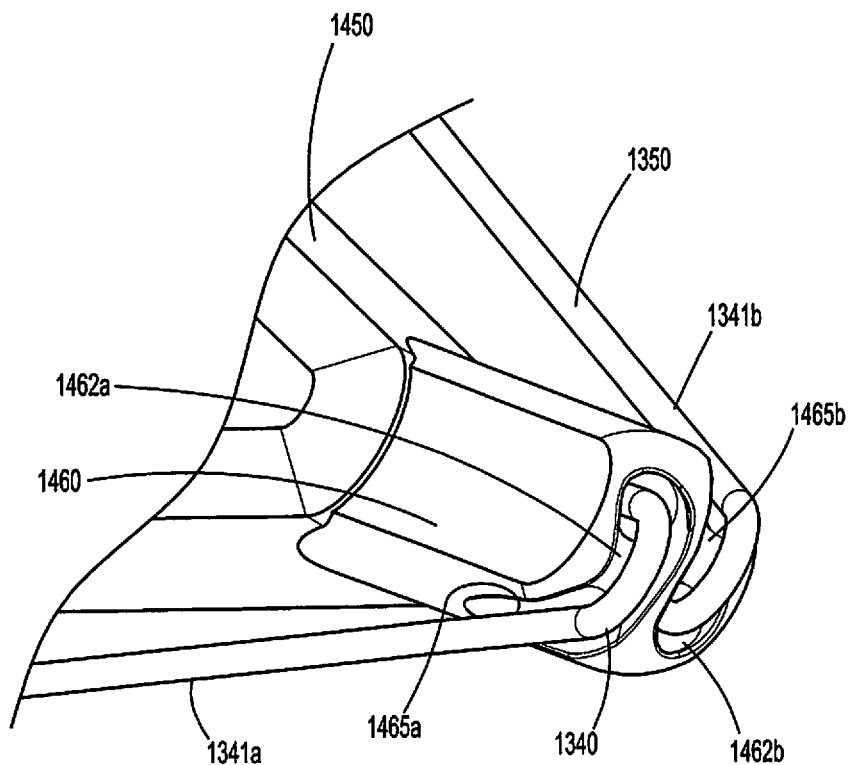
FIG. 15 is a partially enlarged perspective view of a distal portion of the tool assembly of FIG. 12.

With particular reference to FIGS. 14 and 15, a distal portion 1460 of the electrical insulator 1450 defines opposing grooves 1462a, 1462b configured to direct respective first and second segments 1341a, 1341b of the wire portion 1340 in opposing directions towards the respective lateral arms 1454a, 1454b. Such a configuration of the distal portion 1460 of the electrical insulator 1450 provides smooth transition of the wire portion 1340. In this manner, the first segment 1341a of the wire portion 1340 extends through the first channel of the tubular body 1452 of the electrical insulator 1450 and is received in the groove 1462a of the distal portion 1460 of the electrical insulator 1450. The first segment 1341 further extends out of the lateral opening 1465a and into the lateral arm 1454a of the electrical insulator 1450. The second segment 1341b of the wire portion 1340 extends through the second channel of the tubular body 1452 of the electrical insulator 1450 and is received in the groove 1462b of the distal portion 1460 of the electrical insulator 1450. The second segment 1341b further extends out of the lateral opening 1465b and into the lateral arm 1454b of the electrical insulator 1450. Under such a configuration, the first and second segments 1341a, 1341b of the wire portion 1340 are spaced apart and separated from the return lead 1400. Such a configuration enables plunge cutting of tissue by the active lead 1350.

Referring back to FIGS. 13 and 14, the return lead 1400 includes a body 1402 defining a cavity configured to receive at least a portion of the electrical insulator 1450 therein. The body 1402 is tapered along a length thereof. The body 1402 includes a proximal portion 1402a having cutout 1407 dimensioned to securely engage a portion of the sleeve 1500 and to receive the lateral arms 1454a, 1454b of the electrical insulator 1450, as will be discussed below. In addition, the proximal portion 1402a is in communication with the cavity defined in the body 1402. The proximal portion 1402a of the body 1402 further defines opposing lateral slots 1408. The body 1402 further includes a distal portion 1402b defining an aperture 1404 configured to receive the distal portion 1460 of the electrical insulator 1450 therethrough. The lateral arms 1454a, 1454b of the electrical insulator 1450 extend outwardly from the respective lateral slots 1408 of the return lead 1400, and the distal portion 1460 of the electrical insulator 1450 extends out of the aperture 1404 of the return lead 1400.

The sleeve 1500 made of, e.g., polymer or other suitable insulative material, is placed about at least a portion of the stem portion 1352 of the active lead 1350 and a portion of the tubular body 1452 of the electrical insulator 1450 disposed about the neck portion 1354 of the active lead 1350 to securely couple the active lead 1350 and the electrical insulator 1450 thereto. In addition, a proximal portion 1402a of the body 1402 of the return lead 1400 engages a cutout portion 1502 of the sleeve 1500 to securely couple the return lead 1400 to the active lead 1350 and the electrical insulator 1450, while inhibiting electrical communication therebetween.

Figure 16:
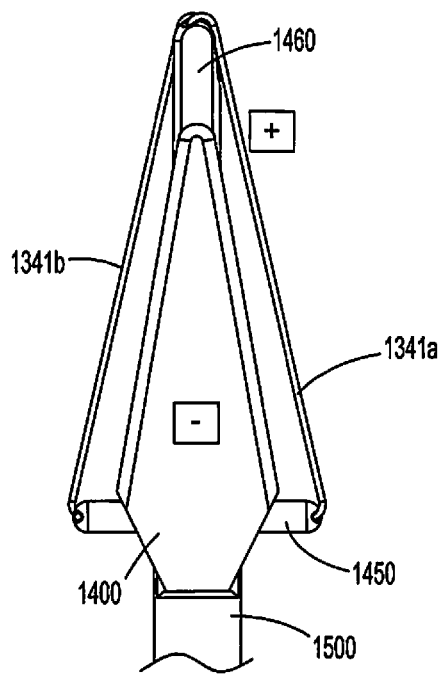
FIG. 16 is a partial side view of the tool assembly of FIG. 12.
Figure 17:
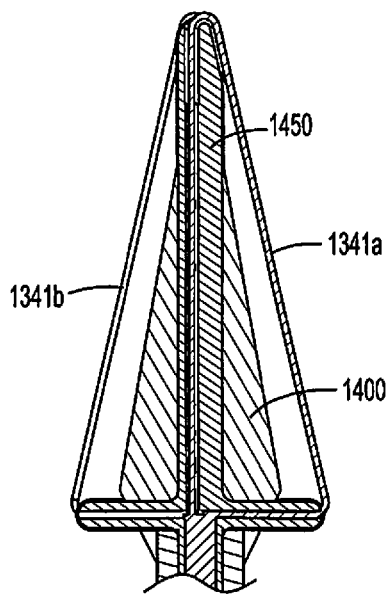
FIG. 17 is a partial side cross-sectional view of the tool assembly of FIG. 12.

With respect to FIGS. 16 and 17, the return lead 1400 may be monolithically formed of stainless steel. Accordingly, any portion of the return lead 1400 may serve as an electrical return for electrosurgical energy (e.g., electric current) conducted through the first or second segments 1341a, 1341b of the active lead 1400. For example, the return lead 1400 may contact tissue at approximately the same time as, e.g., at least one of the first or second segments 1341a, 1341b of the active lead 1400, thus allowing it to cut tissue. The return lead 1400 returns the electrosurgical energy to the electrosurgical energy source. In this manner, the electrosurgical energy applied via the first or second segments 1341a, 1341b across tissue severs tissue in contact with either or both of the first or second segments 1341a, 1341b. The use and operation of the tool assembly 1300 is otherwise substantially similar to the use and operation of the tool assemblies described hereinabove, and thus is not be described herein.

Figure 18:
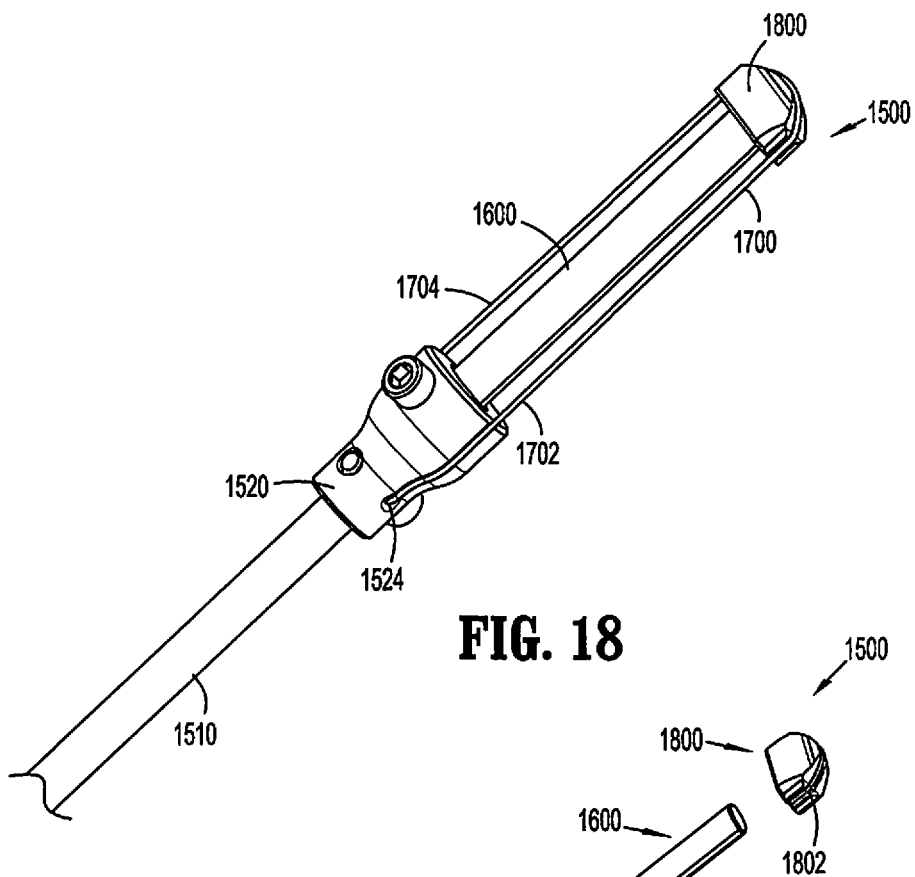
FIG. 18 is a perspective view of a tool assembly for use with an electrosurgical device in accordance with yet another aspect of the present disclosure.
Figure 19:
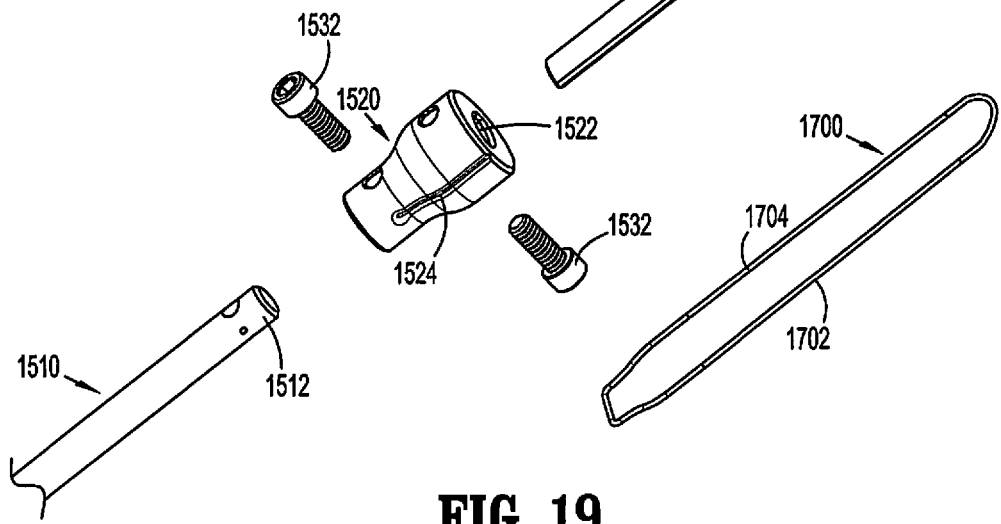
FIG. 19 is an exploded perspective view of the tool assembly of FIG. 18 with parts separated.

With reference now to FIGS. 18 and 19, another tool assembly for use with an electrosurgical device in accordance with an embodiment of the present disclosure is shown generally as a tool assembly 1500. In the interest of brevity, portions of the tool assembly 1500 substantially similar to the portion of the tool assemblies 100, 500, 900 will not be described herein to avoid obscuring the present disclosure in unnecessary detail. The tool assembly 1500 includes an elongate member 1510, a base portion 1520 supported on a distal portion 1512 of the elongate member 1510, a return lead 1600, an active lead 1700, and a cap 1800.

The base portion 1520 is formed from an insulating material such as, e.g., ceramic. The base portion 1520 defines a central bore 1522 and diametrically opposing lateral slits 1524 (only one shown in FIG. 19). Proximal ends of the respective lateral slits 1524 are closed and distal ends of the respective lateral slits 1524 are open. The base portion 1520 further defines first and second bores 1528, 1530 (FIG. 21) to threadably receive respective screws 1532.

The active lead 1700 is in a form of a wire such as, e.g., a single strand tungsten wire. The small surface area of the wire relative to a large surface area of the return lead 1600 provides high efficiency in cutting tissue. The active lead 1700 forms a loop configured to be secured in the diametrically opposing lateral slits 1524 defined in the base portion 1520 such that the first and second segments 1702, 1704 of the active lead 1700 extend out of the respective diametrically opposing lateral slits 1524 of the base portion 1520. In particular, the screw 1532 is threadably inserted into the first bore 1528 between the first and second segments 1702, 1704 to secure the active lead 1700 to the base portion 1520, i.e., within the diametrically opposing lateral slits 1524. A proximal portion 1602 of the return lead 1600 is received in the central bore 1522 of the base portion 1520. The screw 1532 is threadably inserted into the second bore 1530 to secure the return lead 1600 with the base portion 1520. The cap 1800 defines a cavity configured to receive a distal portion 1604 of the return lead 1600. The cap 1800 defines a groove 1802 configured to receive the active lead 1700 therein such that the active lead 1700 wraps around the cap 1800. The cap 1800 is formed of an insulating material such as, e.g., ceramic. The cap 1800 may be coupled with the return lead 1600 by, e.g., friction fit, ultrasonic welding, etc. In addition, the active lead 1700 is in tension to further secure the cap 1800 with the return lead 1600. Under such a configuration, the first and second segments 1702, 1704 of the active lead 1700 define respective gaps with the return lead 1600. A supply line (not shown) connected to the active terminal of the electrosurgical energy source extends through the elongate member 1510 and is electrically coupled to a portion of the active lead 1700 disposed in the base portion 1520. A return line (not shown) connected to the return terminal of the electrosurgical energy source extends through the elongate member 1510 and is electrically coupled to the return lead 1600.

The base portion 1520 and the cap 1800 are formed of a ceramic material due to its hardness and inherent ability to withstand high temperature fluctuations. Alternatively, the base portion 1520 and the cap 1800 may be made from a material having a high Comparative Tracking Index (CTI) having a value in the range of about 300 to about 600 volts. Examples of high CTI materials include nylons and syndiotactic polystryrenes such as QUESTRA® manufactured by DOW Chemical. Other materials may also be utilized either alone or in combination, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

Figure 20:
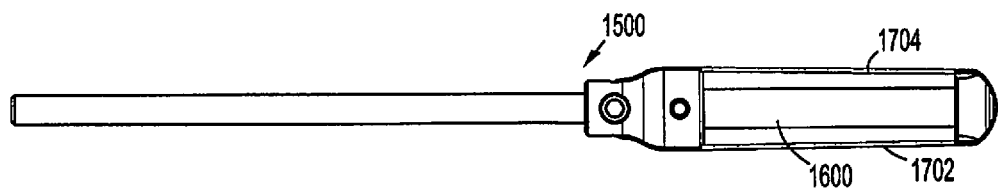
FIG. 20 is a top view of the tool assembly of FIG. 19.
Figure 21:
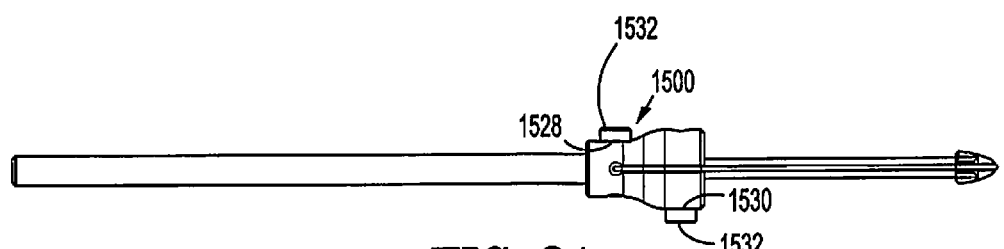
FIG. 21 is a side view of the tool assembly of FIG. 19.
Figure 22:
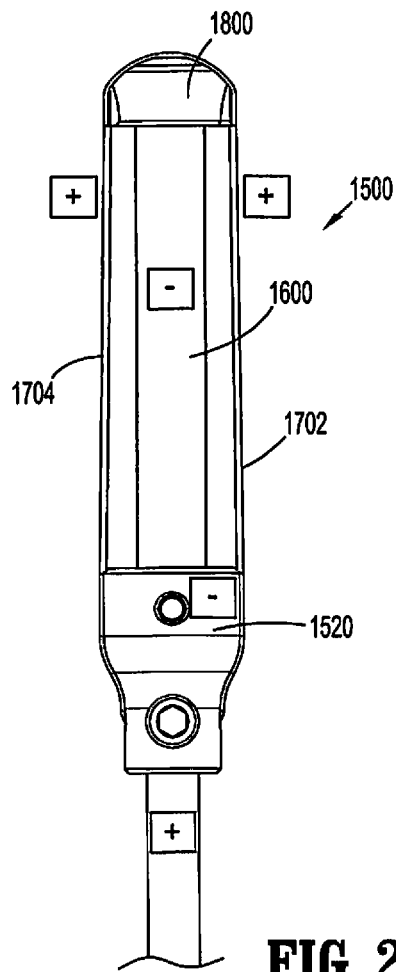
FIG. 22 is a front view of the tool assembly of FIG. 19.

Under such a configuration, the active lead 1700 is spaced apart and insulated from the return lead 1600. The active lead 1700 is configured to cut tissue, and the return lead 1600 serves as an electrical return for electrosurgical energy (e.g., electric current) conducted through the active lead 1700. With reference to FIGS. 20-22, the return lead 1600 may be formed of, e.g., stainless steel. Accordingly, any portion of the return lead 1600 may serve as an electrical return for electrosurgical energy (e.g., electric current) conducted through the first or second segments 1702, 1704 of the active lead 1700. In particular, a large surface area of the return lead 1600 compared to the active lead 1700 may provide a desirable ratio of return surface area to cutting surface area for high efficiency in cutting tissue. For example, the return lead 1600 may contact tissue at approximately the same time as, e.g., at least one of the first or second segments 1702, 1704 of the active lead 1700, and thus allowing the at least one of the first or second segments 1702, 1704 to cut tissue in contact therewith. The return lead 1600 returns the electrosurgical energy to the electrosurgical energy source. In this manner, the electrosurgical energy applied via the first or second segments 1702, 1704 across tissue severs tissue in contact with either or both of the first or second segments 1702, 1704. The use and operation of the tool assembly 1500 is otherwise substantially similar to the use and operation of the tool assemblies described hereinabove, and thus is not be described herein.

The first and second segments 1702, 1704 of the active lead 1700 are provided on opposing sides of the tool assembly 1500. Under such a configuration, the clinician need not rotate the tool assembly 1500 or re-grip the tool assembly 1500 to cut tissue on opposing sides of the surgical site, thereby facilitating cutting of tissue in various directions and orientations.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tool assembly for use with an electrosurgical device for cutting tissue comprising:
   a base portion;
   a return lead adapted to be electrically coupled to a return terminal, the return lead including a body supported on the base portion and defining a bore through the body;
   an electrical insulator extending through the bore of the body, the electrical insulator defining a lumen;
   a center pin extending from the base portion and through the lumen of the electrical insulator, the center pin having a distal portion; and
   an active lead adapted to be electrically coupled to an active terminal, the active lead securely fixed to the base portion and extending between the base portion and the distal portion of the center pin such that a portion of the active lead extends around the distal portion of the center pin and first and second segments of the active lead are spaced apart from the return lead,
   wherein, upon activation, electrosurgical energy is transmitted from the active lead through the tissue to the return lead to cut the tissue in contact with the active lead.

2. The tool assembly according to claim 1, wherein the distal portion of the center pin extends distally from the lumen of the electrical insulator.

3. The tool assembly according to claim 1, wherein the return lead includes a tapered portion and an elongate portion extending distally from the tapered portion.

4. The tool assembly according to claim 3, wherein the tapered portion of the return lead includes opposing first and second surfaces, the first and second segments of the active lead being spaced apart from and extending along the respective opposing first and second surfaces of the return lead.

5. The tool assembly according to claim 4, wherein at least one of the opposing first and second surfaces defines an acute angle with respect to a longitudinal axis defined by the tool assembly.

6. The tool assembly according to claim 1, wherein the active lead is a wire.

7. The tool assembly according to claim 1, wherein the distal portion of the center pin defines a groove configured to guide the portion of the active lead therethrough.

8. The tool assembly according to claim 3, wherein the elongate portion defines opposing lateral slots configured to be in registration with the respective first and second segments of the active lead.

9. The tool assembly according to claim 1, wherein the electrical insulator is formed of ceramic.

10. The tool assembly according to claim 1, wherein the return lead is formed of stainless steel.

11. The tool assembly according to claim 1, wherein the electrical insulator is securely fixed with the base portion.

12. The tool assembly according to claim 11, wherein the return lead is movable relative to the active lead.

13. The tool assembly according to claim 12, wherein the return lead is slidable in a direction orthogonal to a longitudinal axis defined by the tool assembly.

14. The tool assembly according to claim 3, wherein the return lead includes a slidable member coupled to the tapered portion, and the slidable member is slidably disposed within a central cavity of the base portion.

15. The tool assembly according to claim 14, wherein the central cavity of the base portion is dimensioned to enable a predetermined amount of lateral displacement of the slidable member.

16. The tool assembly according to claim 1, wherein the body of the return lead defines a distal opening, a distal end portion of the electrical insulator extends through the distal opening.

17. The tool assembly according to claim 16, wherein the distal end portion of the electrical insulator defines a slot, and the distal portion of the center pin is received within the slot.

18. The tool assembly according to claim 1, wherein the base portion includes lateral bores, and the first segment of the active lead includes a first end anchored in one of the lateral bores and the second segment of the active lead includes a second end anchored in the other of the lateral bores.

19. The tool assembly according to claim 18, wherein the base portion includes anchoring members disposed within the lateral bores, the anchoring members and the center pin adapted to be electrically coupled to the active terminal to supply the electrosurgical energy to the active lead.

20. The tool assembly according to claim 12, wherein the center pin is securely fixed with the base portion.

* * * * *